United States Patent
Tsubota et al.

(10) Patent No.: US 10,799,217 B2
(45) Date of Patent: Oct. 13, 2020

(54) ULTRASOUND IMAGING DEVICE AND ULTRASOUND IMAGE GENERATION PROGRAM

(71) Applicant: HITACHI, LTD., Chiyoda-ku, Tokyo (JP)

(72) Inventors: Yushi Tsubota, Tokyo (JP); Kenichi Kawabata, Tokyo (JP); Atsurou Suzuki, Tokyo (JP); Takahide Terada, Tokyo (JP); Wenjing Wu, Tokyo (JP); Kazuhiro Yamanaka, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 355 days.

(21) Appl. No.: 15/916,788

(22) Filed: Mar. 9, 2018

(65) Prior Publication Data

US 2018/0310919 A1   Nov. 1, 2018

(30) Foreign Application Priority Data

Apr. 26, 2017   (JP) .................. 2017-087507

(51) Int. Cl.
*A61B 8/15*   (2006.01)
*A61B 8/08*   (2006.01)
*A61B 8/00*   (2006.01)

(52) U.S. Cl.
CPC .......... *A61B 8/5207* (2013.01); *A61B 8/0825* (2013.01); *A61B 8/15* (2013.01); *A61B 8/4494* (2013.01); *A61B 8/5269* (2013.01)

(58) Field of Classification Search
CPC ....... A61B 8/5207; A61B 8/0825; A61B 8/15; A61B 8/4494; A61B 8/5269; A61B 8/00
See application file for complete search history.

(56) References Cited

U.S. PATENT DOCUMENTS

| | | | | |
|---|---|---|---|---|
| 4,805,627 A | * | 2/1989 | Klingenbeck | G01N 22/00 324/639 |
| 2013/0204137 A1 | * | 8/2013 | Roy | A61B 8/0825 600/448 |
| 2014/0066772 A1 | * | 3/2014 | West | A61B 8/4494 600/447 |

FOREIGN PATENT DOCUMENTS

| JP | H08508925 A | 2/1996 |
|---|---|---|
| WO | 95/28883 | 11/1995 |

* cited by examiner

*Primary Examiner* — Pascal M Bui Pho
*Assistant Examiner* — Adil Partap S Virk
(74) *Attorney, Agent, or Firm* — Procopio, Cory, Hargreaves & Savitch LLP

(57) ABSTRACT

A sinogram is corrected in a form that can use a straight-ray type reconstruction method while considering trajectory of refracted waves. Specifically, based on the sequentially estimated path information of the virtual waves, an arrival time difference sinogram is corrected by a difference or a ratio between "shortest arrival time of wave" and "arrival time of the wave through the shortest path" to each detection element.

11 Claims, 11 Drawing Sheets

Locus direction: $-\dfrac{dx}{dy} = -\tan\theta = \dfrac{d\Delta t}{dx} C_w$

Cw: sound speed of water

Fig. 9 (c) PRESENT EMBODIMENT

Fig. 9 (b) BENT-RAY RECONSTRUCTION (METHOD OF RELATED ART)

Fig. 9 (a) STRAIGHT-RAY RECONSTRUCTION (METHOD OF RELATED ART)

ULTRASOUND IMAGING DEVICE AND ULTRASOUND IMAGE GENERATION PROGRAM

TECHNICAL FIELD

The present invention relates to an ultrasound imaging device.

BACKGROUND ART

An ultrasound computed tomography (CT) device is a device for irradiating an object in a medium with ultrasound waves from a plurality of directions and for tomographic-imaging material property (sound speed and attenuation rate) on the inside of the object from signals transmitted through the object. The ultrasound waves are generated using piezoelectric elements. Piezoelectric elements are arranged in a ring array, and the object is inserted in an opening of the ring array and photographed.

PTL 1 discloses a basic configuration and an imaging technology of the ultrasound CT.

CITATION LIST

Patent Literature

PTL 1: JP-T-08-508925

SUMMARY OF INVENTION

Technical Problem

Ultrasound waves are refracted at the boundary between two regions with different refractive indices when transmitting through an object. Therefore, when reconstructing a material property image from a transmission wave without considering the refraction of the ultrasound wave, the boundary of the material property image becomes unclear, and the error increases. In order to improve the image quality, it is necessary to reconstruct the image in consideration of the influence of the refraction, but the computation amount increases and the computation costs are high. For example, as a method of reconstructing an image in consideration of the influence of refraction, there is a Bentley type sequential reconstruction method, but a lot of memory capacity and computation time are required for creating a projection matrix (system matrix) for reconstruction.

An object of the present invention is to reduce the material property error and computation costs in the reconstruction image derived from the refraction of the transmission wave.

Solution to Problem

In order to achieve the object, according to the present invention, the following ultrasound imaging device is provided. In other words, there is provided an ultrasound imaging device including: an ultrasound transceiver element array which irradiates an object with ultrasound waves from a plurality of directions, and receives a transmission wave that has been transmitted through the object; an image generation section which acquires an arrival time difference of the transmission waves in a case where there is the object and in a case where there is no object to the ultrasound transceiver element array from a received signal of the ultrasound transceiver element array, and reconstructs a material property distribution image of the inside of the object based on the arrival time difference; and a correction section which corrects the arrival time difference, based on an arrival time of virtual transmission waves that reach at least one element of the ultrasound transceiver element array through a path that achieves the shortest arrival time, which is calculated based on material property distribution indicated by the material property distribution image ("shortest arrival time of the virtual wave"), and the arrival time of virtual transmission waves that reach the same element through the shortest geometrical path ("arrival time of the virtual wave through the shortest path").

Advantageous Effects of Invention

According to the present invention, it is possible to reduce the material property error and computation costs in the reconstruction image derived from the refraction of the transmission wave.

BRIEF DESCRIPTION OF DRAWINGS

FIG. 5(a) is the entire flow of image reconstruction from transmission wave signal reading to corrected image generation, FIG. 5(b) is a processing flow specifically illustrating calculation of the refraction path of the wave, and FIG. 5(c) is a processing flow specifically illustrating the correction processing of a sinogram.

DESCRIPTION OF EMBODIMENTS

An ultrasound imaging device according to one embodiment of the present invention will be described with reference to the drawings.

In the present invention, a sinogram is corrected in a form that can use a straight-ray type reconstruction method while considering trajectory of refraction of transmission waves. Specifically, based on the estimated path information of the virtual waves, an arrival time difference sinogram is corrected by a difference or a ratio between the "shortest arrival time of the virtual wave" and the "arrival time of the virtual wave through the shortest path" to each detection element. Hereinafter, the present invention will be described.

Figure 1:
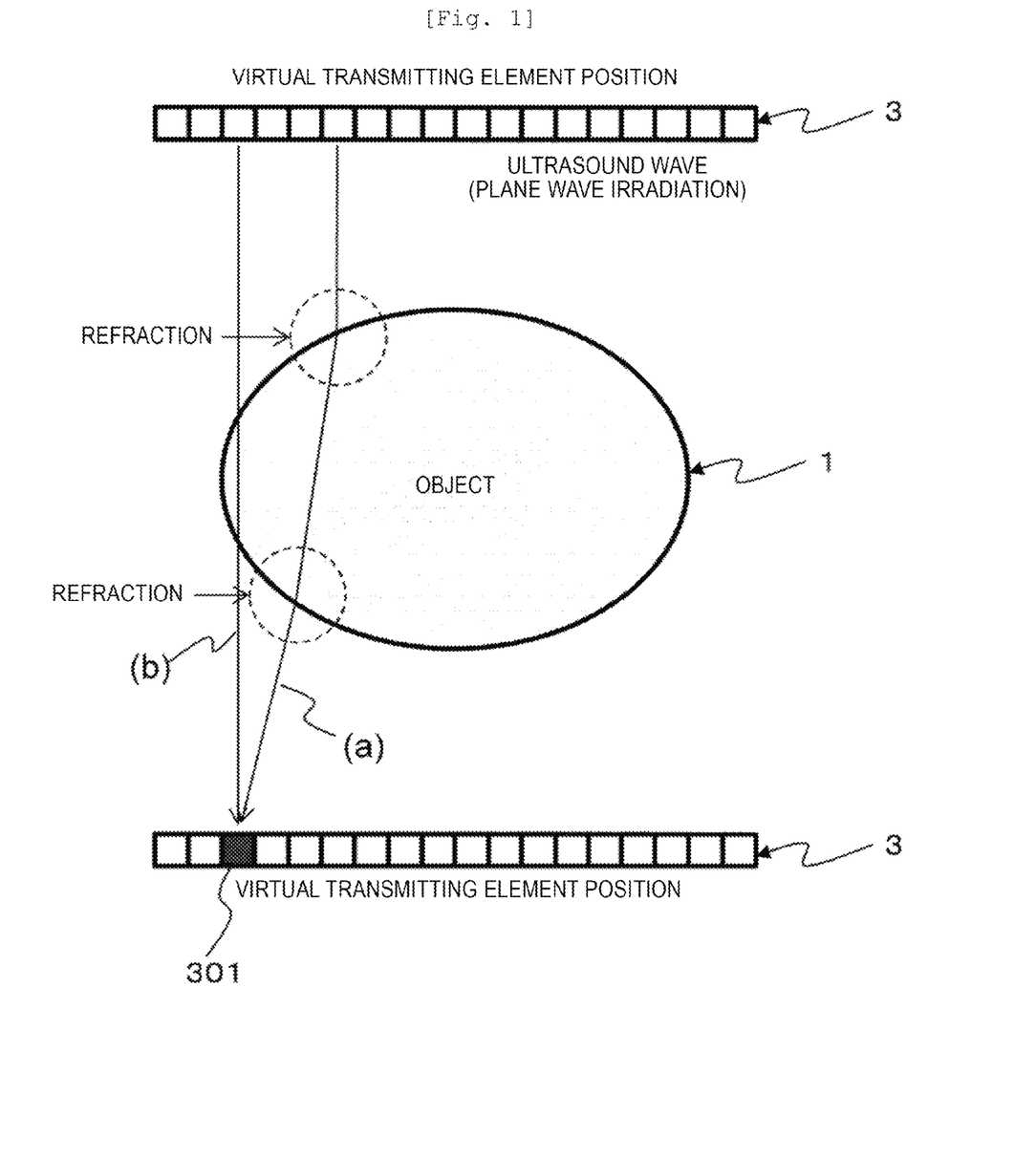
FIG. 1 is an explanatory view illustrating a refraction path (a) and a straight path (b) for describing a correction method of an ultrasound imaging device according to an embodiment of the present invention.

FIG. 1 is an explanatory view illustrating the principle of the present invention. As illustrated in FIG. 1, an ultrasound imaging device of the embodiment includes: an ultrasound transceiver element array 3 which irradiates an object 1 with ultrasound waves from a plurality of directions, and receives a transmission wave that has been transmitted through the object 1; an image generation section which reconstructs a material property distribution image of the inside of the object 1 based on an arrival time difference dT in a case where there is the object and in a case where there is no object in the transmission wave received in the ultrasound transceiver element array 3; and a correction section.

The correction section corrects the arrival time difference dT, based on the arrival time of virtual transmission waves that reach one element 301 of the ultrasound transceiver element array 3 through a path (a) that achieves the shortest arrival time, which is calculated based on the material property distribution indicated by the material property distribution image ("shortest arrival time of the virtual wave Ta"), and the arrival time of virtual transmission waves that reach the same element 301 through the shortest geometrical path (b) ("arrival time of the virtual wave through the shortest path Tb").

The path (a) that achieves the shortest arrival time Ta is a path along which the transmission wave advances while being refracted in accordance with the material property distribution indicated by the material property distribution image. Meanwhile, the shortest geometric path (b) is a path assumed that the transmission wave goes straight without refraction regardless of the material property distribution. Accordingly, based on the difference (difference or ratio) between the "shortest arrival time of the virtual wave Ta" that passes through the path (a) and the "arrival time of the virtual wave through the shortest path Tb" that passes through the path (b), by correcting the arrival time difference dT in a case where there is the object and in a case where there is no object using the reconstruction, even in a case where the image generation section uses the straight-ray type reconstruction method, it is possible to obtain an image considering refraction of the transmission wave.

In other words, since the arrival time of the transmission wave actually received by the ultrasound transceiver element array 3 is time of the transmission wave arrived at the ultrasound transceiver element array 3 through refraction paths in accordance with the actual material property distribution of the object 1, the path is close to the path (a). Therefore, when reconstructing a sinogram configured of the arrival time difference Td acquired from the arrival time of the actual transmission wave using the straight-ray type reconstruction method, the error of the reconstructed image becomes large. In the embodiment, the correction section corrects the arrival time difference dT based on the difference between the "shortest arrival time of the virtual wave Ta" and the "arrival time of the virtual wave through the shortest path Tb" which are obtained by calculation, and accordingly, it is possible to reduce the error of the reconstructed image while using the straight-ray type reconstruction method with a small computation amount, and to obtain a reconstructed image close to a case of using the bent-ray type reconstruction method with a large computation amount.

Furthermore, in other words, the "shortest arrival time of the virtual wave Ta" is a first arrival time calculated on the assumption that the transmission wave reaches one element 301 of the ultrasound transceiver element array 3 while refracting in accordance with the material property distribution indicated by the material property distribution image, and the "arrival time of the virtual wave through the shortest path Tb" is a second arrival time calculated on the assumption that the transmission wave goes straight and reaches the same element 301. The correction section corrects the arrival time difference dT based on the first arrival time and the second arrival time.

Hereinafter, the ultrasound imaging device according to the embodiment of the present invention will be described more specifically.

Among the ultrasound imaging devices, a device for irradiating an object with ultrasound waves from a plurality of directions and for tomographic-imaging the material property (sound speed and attenuation rate) of the inside of the object from signals transmitted through the object, is called an ultrasound computed tomography scanner. Unlike mammography, the ultrasound computed tomography scanner is not exposed to radiation, and thus, the ultrasound computed tomography scanner is expected to be a breast cancer screening device which can be employed to younger people. Hereinafter, an aspect of utilizing the present invention for a breast cancer screening device will be described, but a target to be photographed is not particularly limited.

Figure 2:
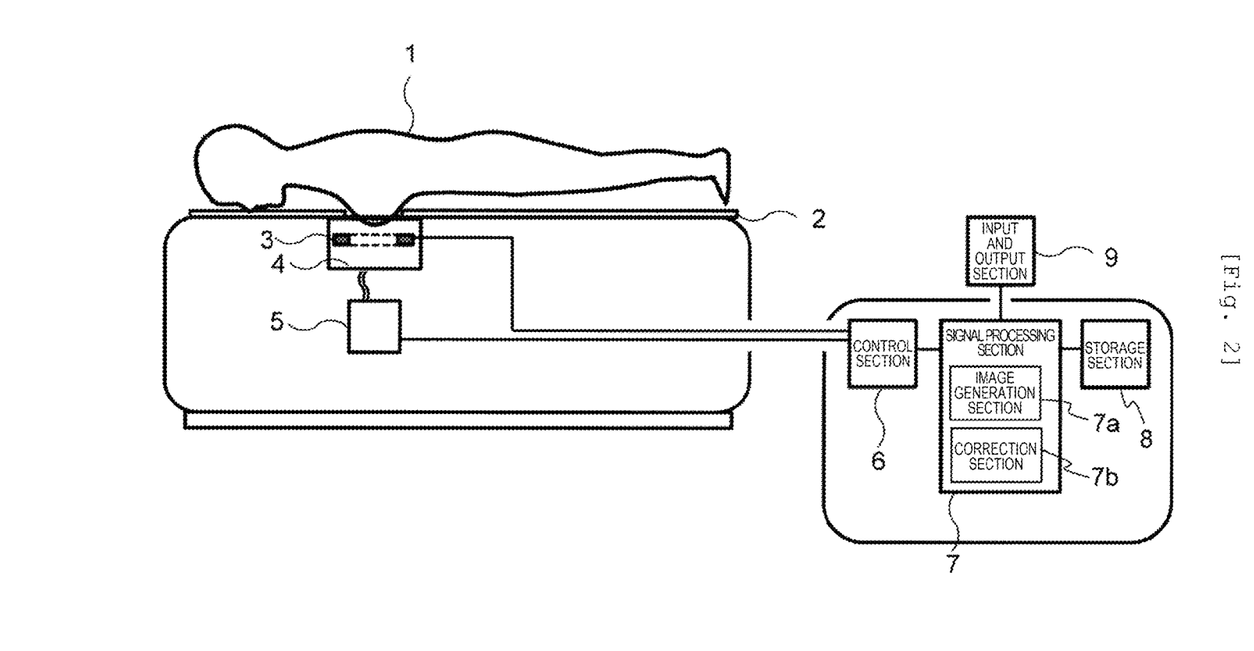
FIG. 2 is a block diagram illustrating a schematic structure of a sagittal section of an ultrasound imaging device (ultrasound computed tomography scanner) according to the embodiment of the present invention.
Figure 3:
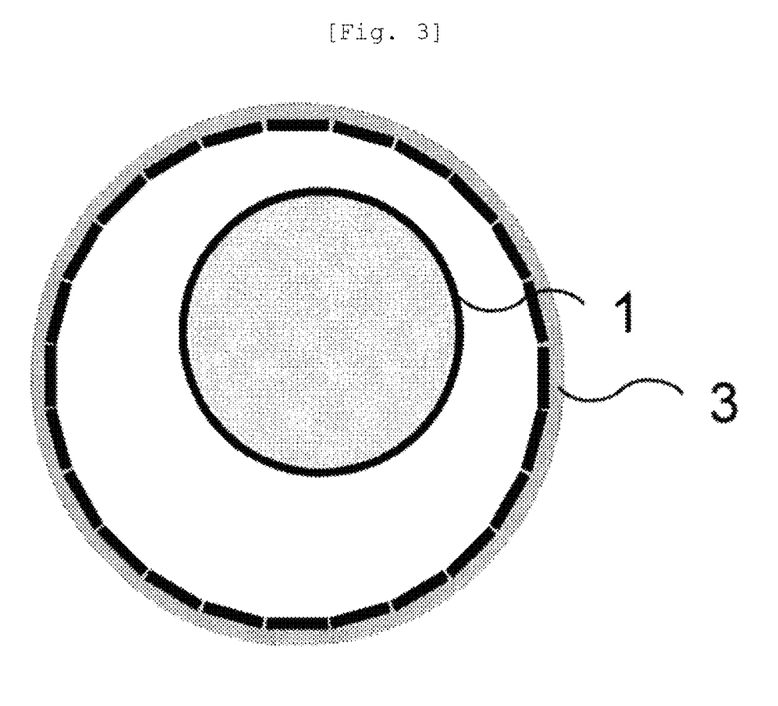
FIG. 3 is an explanatory view illustrating a schematic structure of a coronal section of a ring array used in the embodiment.

FIG. 2 is a schematic structure of a sagittal section of the ultrasound computed tomography scanner according to the present invention. In a bed 2 on which the patient 1 is placed, an opening 2a for inserting a chest is provided, and a columnar water tank 4 is disposed below the opening 2a. On the inside thereof, a ring-shaped ultrasound transceiver element array (hereinafter referred to as a ring array) 3 illustrated in FIG. 3 is provided so as to be movable in parallel in the axial direction of the water tank 4. In the ring array 3, a plurality of piezoelectric elements (ultrasound elements) which are ultrasound transceivers are disposed in a circular shape. The water tank 4 is filled with warm water. A reserve tank 5 is connected to the water tank 4. The reserve tank 5 has a function of purifying hot water of the water tank 4, overheating, and degassing.

A control section 6 and a signal processing section 7 are connected to the ring array 3 and the reserve tank 5. In the signal processing section 7, an image generation section 7a and a correction section 7b are provided. An input and output section 9 and a storage section 8 are connected to the signal processing section 7.

The signal processing section 7 is configured of a computer or the like including a processor, such as a central processing unit (CPU) or a graphics processing unit (GPU), and a memory, and as the CPU reads and executes a program stored in the memory, the function of the image generation section 7a and the correction section 7b of the signal processing section 7 is realized by software. In addition, a part or the entirety of the signal processing section 7 can also be realized by hardware. For example, the signal processing section 7 may be configured by using a custom IC, such as application specific integrated circuit (ASIC), or a programmable IC, such as field-programmable gate array (FPGA), and a circuit design may be performed so as to realize the operation of the image processing section 7a and the correction section 7b of the signal processing section 7.

The photographing conditions of the ultrasound computed tomography scanner are set by the user through a touch panel of the input and output section 9 or the keyboard. The set conditions and the like are saved in the memory of the storage section 8, the hard disk drive or the like. Based on the conditions, a control signal processed by the central processing unit (CPU) and the like of the signal processing section 7 is sent to various controllers disposed in the control section 6. The controller performs transmission and reception or switching of ultrasound signals by each ultrasound element of the ring array 3, control of vertical movement of the ring array 3, water pressure control by the reserve tank 5, temperature control of hot water, and the like. Received signals of each ultrasound element of the ring array 3 are recorded in the storage section 8 and image processing operations, such as image reconstruction, are executed in the signal processing section 7. As information on a tomographic image or the like of the reconstructed patient 1, information is displayed on a monitor or the like of the input and output section 9. The control section 6, the signal processing section 7, and the storage section 8 can also be accommodated in the space in a lower portion of the bed 2.

Figure 4:
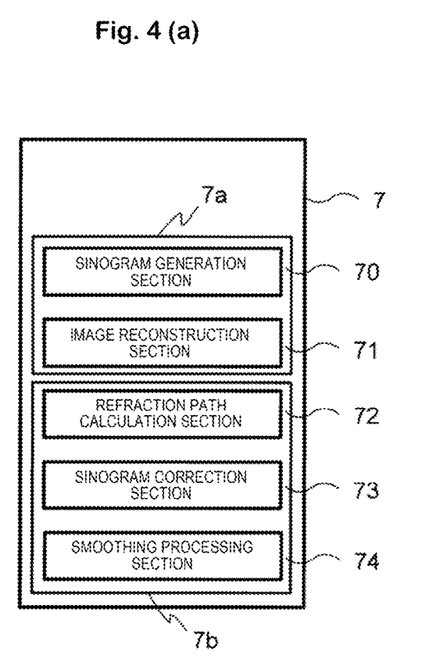
FIG. 4(a) is a block diagram illustrating a main configuration of a signal processing section of the device of FIG. 2.
FIG. 4(b) is a block diagram illustrating a main configuration of a refraction path calculation section of the signal processing section.

As illustrated in FIG. 4(a), the image generation section 7a of the signal processing section 7 includes a sinogram generation section 70 and an image reconstruction section 71, and the correction section 7b includes a refraction path calculation section 72, a sinogram correction section 73, and a smoothing processing section 74. Furthermore, as illustrated in FIG. 4(b), an arrival time distribution generation section 720, an arrival time difference distribution generation section 721, an arrival time difference distribution differentiation section 722, and a smoothing processing section 723 are provided in the refraction path calculation section 72 of the correction section 72. The operations of each of the sections will be described later.

With such a configuration, it becomes possible to display a tomographic image of the patient 1 in the water tank 4.

Hereinafter, an example of the inspection procedure will be described below. Preliminary inquiry and clothe change to examination clothe of the patient 1 is finished. After this, the patient enters the examination room, lies face down on the bed 2, and inserts one breast into the water tank 4 filled with hot water. In addition, ultrasound CT measurement is performed as will be described below, and the other breast is measured in the same manner.

Hereinafter, an example of a specific configuration of the device and the measurement procedure will be described. When the center frequency of the ultrasound waves radiated from each ultrasound element of the ring array 3 is 1.5 MHz, the wavelength of the ultrasound wave in water is about 1 mm. When the pitch of the ultrasound elements (piezoelectric elements) is 0.5 mm, the ring array 3 having a diameter of 326 mm is configured with 2048 channels of piezoelectric elements. After the control section 6 drives the ultrasound elements of 512 channels of the ring array 3, and radiates the ultrasound waves of the plane wave of which the phases are arranged, the control section 6 receives the reflection wave by the same ultrasound elements of 512 channels, and receives the transmission wave by the ultrasound element of 512 channels at a position opposing the transmitted ultrasound element. Accordingly, it is possible to ensure a photographing field of view (FOV) as a circle having a diameter of 230 mm. As the control section 6 shifts the piezoelectric elements of 512 channels driven on the ring array 3 by 4 channels, radiates the plane wave, receives the reflection wave and the transmission wave, and repeats the reception of reflection wave and the transmission wave, it is possible to obtain signals of the transmission wave and the reflection wave from 360 degrees around the object 1 with respect to 512 views with an angle shifted by 0.7 degrees. When the thickness of the water tank 4 in the axial direction of the piezoelectric element is 10 mm, data of 40 slices can be obtained with a displacement of 200 mm by repeating the photographing by displacing the ring array 3 with a pitch of 5 mm in the axial direction of the water tank 4. The above-described procedure is performed with respect to a state where the object 1 is inserted and a state where the object 1 is not inserted, and reconstructs an image for each slice based on the obtained received signal (the transmission wave signal and the reflection wave signal), and accordingly, three-dimensional information of breast of the patient 1 is obtained.

Hereinafter, an example of a processing method of the transmission wave signal will be described. FIG. 5(a) is a processing flow from data reading performed by the signal processing section 7 to completion of correction in order to correct the influence of refraction of the material property image. FIG. 5(b) illustrates a processing flow related to the calculation of the refraction path of the wave of FIG. 5(a), and FIG. 5(c) illustrates a processing flow related to the sinogram correction. FIG. 6(a) illustrates a sinogram in which the arrival time difference dT is arranged in the channel direction and in the view direction, and FIG. 6(b) illustrates the material property distribution (sound speed distribution) image reconstructed from the sinogram of FIG. 6(a).

Figure 5:
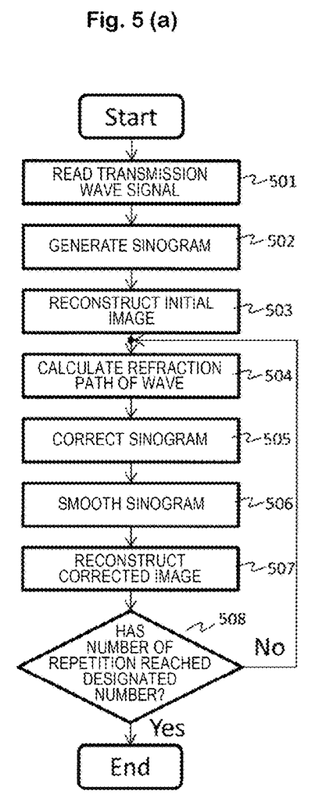
FIG. 5 is a processing flow in the signal processing section of the embodiment.
Figure 6:
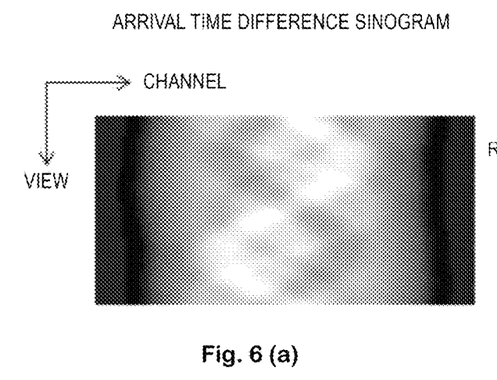
FIG. 6(a) is a diagram illustrating a sinogram of an arrival time difference.
FIG. 6(b) is an example of a reconstructed image (sound speed image).

Hereinafter, in particular, a procedure for reconstructing a tomographic image (material property distribution image) from the received data of the transmission wave will be described with reference to FIGS. 5 and 6. Here, the material property are assumed to be sound speed, but the physically equivalent refractive index or the distribution of the slowness may be obtained.

First, the sinogram generation section 70 of the image generation section 7a reads the received signal of the transmission wave measured by the ultrasound element, performs Hilbert transformation in the time direction, and acquires the arrival time (timing) of a peak position of the received signal (step 501). The sinogram generation section 70 calculates the arrival time difference dT of the peak positions of the received signals before and after the insertion of patient 1 for each projection angle (view) and each receiving element (channel). The arrival time difference dT is arranged in the channel direction and in the view direction as illustrated in FIG. 6(a), and a sinogram is generated (step 502). The sinogram is obtained for each slice.

The image reconstruction section 71 performs filtered back projection (FBP) or iterative reconstruction which is widely used in the field of X-ray CT to each sinogram, and accordingly, the image reconstruction section 71 reconstructs a tomographic image (initial image) (step 503). From the sinogram of the arrival time difference dT of the received wave, the image indicating the distribution of the difference in delay before and after the insertion of the patient 1 is reconstructed. Since the delay is a reciprocal of the sound speed and the sound speed of water is known, a sound speed image (FIG. 6(b)) indicating the distribution of the sound speed of the patient 1 can be obtained from the image indicating the distribution of the difference in delay.

Next, the refraction path calculation section 72 of the correction section 7b calculates the above-described path (a) which achieves the shortest arrival time and the shortest geometrical path (b) from the sound speed image (hereinafter, referred to as the initial sound speed image) reconstructed by the image reconstruction section 71 (step 504). An example of the calculation method is illustrated using the flow in FIG. 5(b) and FIG. 7.

First, the refraction path calculation section 72 reads the initial sound speed image (FIG. 7(a)) from the storage section 8 (step 511), and the spatial distribution (FIG. 7(b)) at arrival time t1 of the virtual wave (transmission wave) at an arbitrary position in the FOV field from the transmitting element to the receiving element (step 512). In other words, in a case where the refraction path calculation section 72 assumes that the sound speed distribution indicated by the initial sound speed image is within the FOV, and transmits the ultrasound waves from the plurality of ultrasound elements (transmitting elements) 3a of the ultrasound transceiver element array 3 to the FOV, the spatial distribution of the time t1 at which the transmission wave of the ultrasound wave reaches each point in the FOV is acquired by calculation. Here, since the arrival time of the ultrasound transmission wave is calculated by assuming the sound speed distribution, the transmission wave is called a virtual wave. Specifically, the arrival time of the virtual wave is acquired using a method of solving the eikonal equation (first marching method) or the like.

In addition, the disposition of the transmitting elements of the ultrasound transceiver element array 3 assumed in the calculation may be a virtual one which is different from the actual one. In the example illustrated in FIG. 7(b), on the assumption that the ultrasound transceiver element array 3 is not in a ring shape, a plurality of transmitting elements 3a and a plurality of receiving elements 3b are respectively arranged linearly and oppose each other across the FOV, the spatial distribution of the ultrasound wave arrival time t1 is acquired.

Similarly, the refraction path calculation section 72 acquires the spatial distribution (FIG. 7(d)) of arrival time t2 of the virtual wave based on the sound speed distribution (FIG. 7(c)) in a case where the object 1 is not disposed (step 512).

In addition, the refraction path calculation section 72 generates a spatial distribution of an arrival time difference Δt (FIG. 7(e)) by taking the difference Δt between arrival times t1 and t2 with and without the object 1 (step 513).

Next, the refraction path calculation section 72 differentiates the spatial distribution of the arrival time difference Δt in the direction (the direction is considered as an x direction) perpendicular to the advancing direction (the direction is considered as a y direction) of the virtual plane wave ignoring the refraction (step 514). An image which indicates the obtained differentiated values (dΔt/dx) of each point with gradation is illustrated in FIG. 7(f). The refraction path calculation section 72 smooths the obtained result (dΔt/dx) as necessary.

Figure 8:
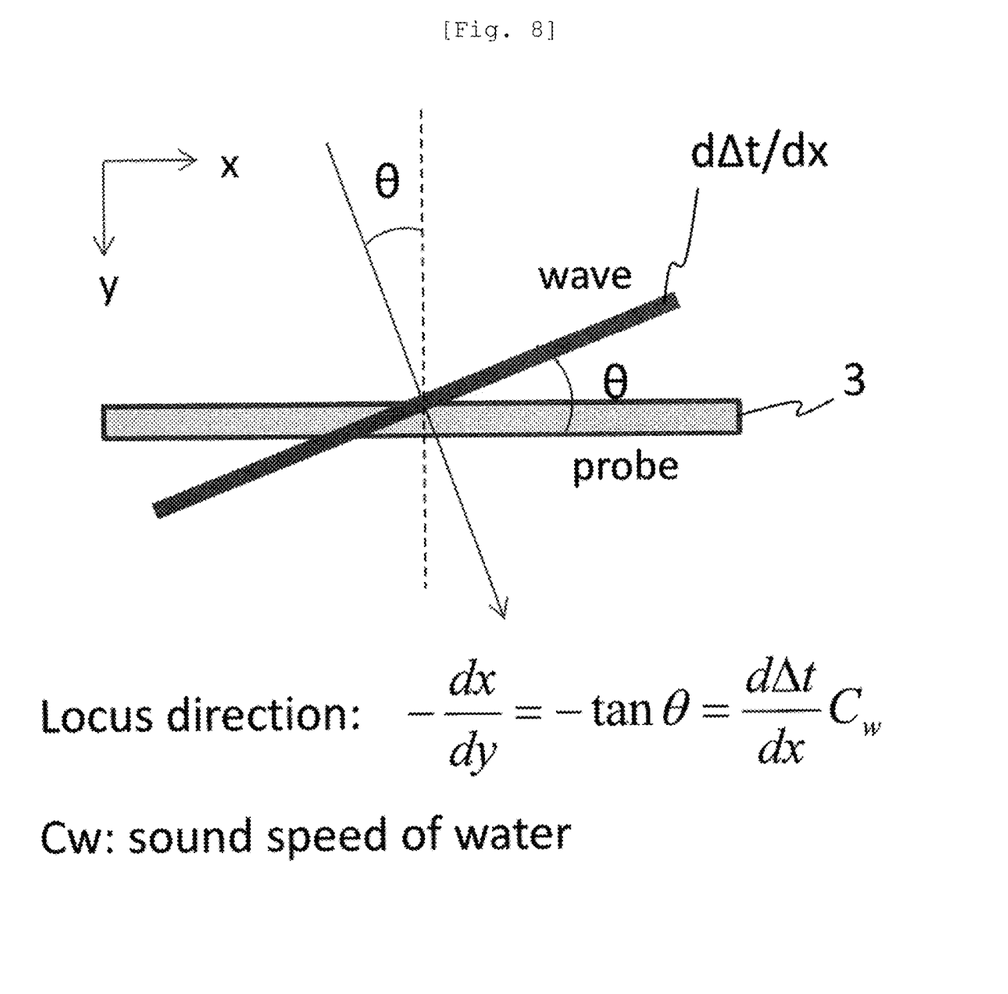
FIG. 8 is a view for describing a relationship between the differentiation result of the distribution of the arrival time difference and an advancing direction of the wave.

The obtained differentiated value (dΔt/dx) represents the advancing direction (the inclination from the y direction is θ) of the virtual wave at each point in the FOV, as is apparent from the equation (1) and FIG. 8. Accordingly, by solving the equation (1), the paths of the refracted waves from the position of the receiving element 3b to the position of the transmitting element 3a can be respectively estimated (step 515). In the equation (1), Cw indicates the sound speed value of water. In addition, the method of acquiring the path of the refracted wave is not limited to the one illustrated here.

$$\frac{dx}{dy} = \tan\theta = -\frac{d\Delta t}{dx}C_w \qquad \text{[Equation 1]}$$

Figure 7:
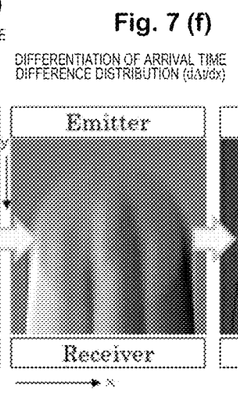
FIG. 7(a) is a view illustrating an example of an initial sound speed image in a case where there is an object.
FIG. 7(b) is a view illustrating distribution of arrival times of ultrasound waves to each point of FOV where there is sound speed distribution indicated by the image of FIG. 7(a)
FIG. 7(c) is a view illustrating an example of an initial sound speed image in a case where there is no object.
FIG. 7(d) is a view illustrating distribution of arrival times of ultrasound waves to each point of the FOV where there is the sound speed distribution indicated by the image of FIG. 7(c)
FIG. 7(e) is a view illustrating the distribution of the the arrival time difference of FIG. 7(b) and the arrival time of FIG. 7(d)
FIG. 7(f) is a view illustrating a differentiation result of the distribution of the arrival time difference of FIG. 7(e) in an x direction.
FIG. 7(g) is a view illustrating a superimposed image of a path (refraction path) which achieves the shortest arrival time to the ultrasound element drawn based on the differentiation result of FIG. 7(f), and the initial sound speed image, respectively.

An example of a method of acquiring the path of the refracted wave will be described more specifically. First, the angle θ is acquired by the equation (1) from the differentiated value (dΔt/dx) of a pixel which is the closest to the center of one receiving element 3b in the image of FIG. 7(f), and the path of an angle θ is drawn in the region of the pixel. Next, among the pixels which surround the pixel that draws the path, the pixel reached by the drawn path is selected, and the path of the angle θ acquired from the differentiated value (dΔt/dx) is drawn in the region of the pixel. By repeating the process until reaching any of the transmitting elements 3a, it is possible to draw the path that reaches one receiving element 3b while the plane wave refracts in accordance with the sound speed with respect to the FOV where there is the sound speed distribution indicated by the sound speed image of FIG. 7 (a). The path is the path (a) of the transmission wave (virtual wave) that reaches one element 301 of the ultrasound transceiver element array 3 of FIG. 1 in the shortest arrival time. Regarding all of the receiving elements 3b, as illustrated in FIG. 7(g), the path (path (a)) of the refracted wave is acquired.

The sinogram correction section 73 corrects the sinogram generated in step 502, in step 505 of FIG. 5(a). The processing will be described with reference to the flow of FIG. 5(c).

The sinogram correction section 73 reads the sinogram generated in step 502, the initial image (initial sound speed image) generated in step 503, and the path (a) of the refraction wave generated in step 504 (step 521).

The sinogram correction section 73 calculates an arrival time $T^{BR}_{sim}$ (="shortest arrival time of the virtual wave Ta") through the path (a) for each projection angle (view) and each receiving element (channel) (step 522). Specifically, the sinogram correction section 73 extracts each sound speed C(x) of each point (pixel) along the path (a) on the initial sound speed distribution image. The sinogram correction section 73 calculates the arrival time $T^{BR}_{sim}$ through the path (a) of the refracted wave by calculating the arrival time T of the equation (4) using the sound speed C(x) of each point. The equation (4) is a numerical formula for acquiring a time dx/C(x) required for the refracted wave (virtual wave) to pass through the region that corresponds to one pixel by dividing the size (dx) of the region of the object 1 that corresponds to one pixel by the sound speed C(x), and for acquiring an arrival time T by integrating the time dx/C(x) with respect to each point along the path (a).

In addition, the sinogram correction section 73 calculates an arrival time $T^{SR}_{sim}$ (="arrival time of the virtual wave through the shortest path Tb") of the virtual transmission wave that reaches the receiving element through the shortest geometrical path (b) for each projection angle (view) and each receiving element (channel) (step 522). Specifically, first, the sinogram correction section 73 sets the shortest path (b) as illustrated in FIG. 1. The shortest path (b) is a path having a straight line that connects a certain receiving element 3b (301) and any of the rows of the transmitting elements 3a, and is the path having the shortest distance. Next, the sinogram correction section 73 extracts each sound speed C(x) of each point (pixel) along the path (b) on the initial sound speed distribution image, and calculates the arrival time $T^{SR}_{sim}$ using the equation (4).

The sinogram correction section 73 calculates a difference ($T^{BR}_{sim} - T^{SR}_{sim}$) or a ratio ($T^{BR}_{sim}/T^{SR}_{sim}$) between the arrival time $T^{BR}_{sim}$ of the virtual wave which passes through the path (a) of the refracted wave and the arrival time $T^{SR}_{sim}$ of the virtual wave which passes through the shortest geometrical path (b) (step 523). By using the acquired difference or ratio, an arrival time difference $dT^{BR}_{exp}$ (=dT) of the received signal of the sinogram generated in step 502 is corrected by the equation (2) or equation (3) (step 524). Accordingly, the sinogram correction section 73 corrects the arrival time difference $dT^{BR}_{exp}$ (=dT) of the actual received signal of the sinogram generated in step 502 to an arrival time difference $dT^{SR}_{exp}$ that corresponds to the straight-ray.

$$dT^{SR}_{exp} = dT^{BR}_{exp} - (T^{BR}_{sim} - T^{SR}_{sim}) \quad \text{[Equation 2]}$$

$$dT^{SR}_{exp} = dT^{BR}_{exp} \times \frac{T^{SR}_{sim}}{T^{BR}_{sim}} \quad \text{[Equation 3]}$$

$$T = \int_{path} \frac{dx}{C(x)} \quad \text{[Equation 4]}$$

Next, the smoothing processing section 74 smooths the sinogram after being corrected in step 505 as necessary (step 506).

The image reconstruction section 71 of the image generation section 7a performs correction in steps 505 and 506, and reconstructs the sinogram smoothed as necessary with FBP or the like (step 507). Accordingly, it is possible to obtain a sectional image (sound speed image) of the sound speed after the correction of which an error of the material property (sound speed) in the reconstructed image derived from refraction of the transmission wave is reduced. The obtained sound speed image after the correction is displayed on the monitor of input and output section 9 and stored in the storage section 8.

By the above-described steps, the flow of FIG. 5(a) may be ended, but further, steps 504 to 507 may be repeatedly and sequentially applied using the sound speed image after the correction. Hereinafter, in particular, an example of a method for sequentially applying the correction method will be described.

Based on the obtained sound speed image after the correction in step 507, the path (a) of the refracted wave is calculated again (step 504), the sinogram corrected in the previous step 505 is corrected again (step 505), the sinogram is smoothed as necessary (step 506), and the sound speed image is reconstructed based on the recorrection and the sinogram smoothed as necessary (step 507). By repeating the series of processing, it is possible to sequentially correct errors caused by the refraction. The sequential processing is stopped after executing the number of repetitions designated in advance by the user (step 508). Otherwise, with respect to the region of interest on the image of which the setting is received from the user via the input and output section 9, the signal-to-noise ratio (S/N) is acquired, and in a case where the value of the S/N is equal to or greater than a value set by the user in advance, or in a case where the rise width from the S/N of the original image before the repetition of the correction becomes equal to or less than a threshold value determined in advance by the user, the operation may be configured to be stopped. In addition, the stop conditions may be set so that recommended values are automatically set without designation of the user.

In this manner, by repeating the correction of the embodiment, it is possible to obtain a sectional image (sound speed image) of the sound speed after the correction of which an error of the material property (sound speed) in the reconstructed image derived from refraction of the transmission wave is further reduced.

The reason why the image reconstruction method of the embodiment described above has a lower computation load than that of the method of the related art will be described. The bent-ray image reconstruction of the related art is performed by using a sequential approximation method, such as an algebraic reconstruction technique (ART). The projection matrix (system matrix) which indicates the relationship between the image and the projection is generally a huge matrix, and the calculation thereof is heavily loaded. However, usually, when the geometry of the measurement system is once determined, the projection matrix is precomputable and invariant, and thus, this does not cause a large problem. However, in a case of considering the refraction path which depends on the sound speed distribution of the object, the projection matrix cannot be calculated in advance, and it is necessary to recalculate every time when the sound speed distribution is updated in the course of the sequential approximation processing. This is the first factor to increase the calculation load in consideration of refraction in the method of the related art.

In the image reconstruction method of the embodiment, by performing the correction to reduce the influence of refraction on data (arrival time difference dT) which configures the sinogram, and by performing a projection operation assuming a straight-ray model, the computation load caused by the projection operation is reduced. By the method, even in a case where the numerical image reconstruction method, such as a sequential approximation method, is used, it is possible to perform the computation faster than that in the related art while considering the refraction. In addition, when the sinogram after the correction is used, an analytical image reconstruction method, such as FBP, can also be used, and further speed-up is possible.

Figure 9:
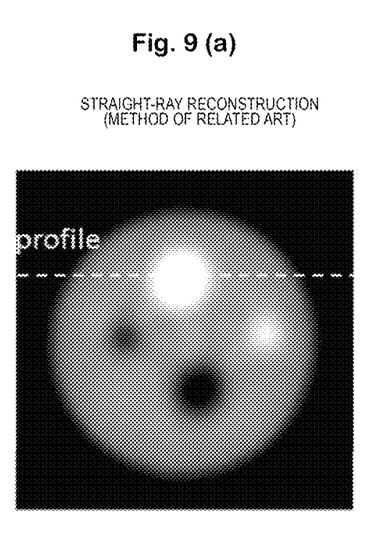
FIG. 9 is an example of the sound speed images which are respectively generated by (a) a straight-ray reconstruction method, (b) a bent-ray reconstruction method, and (c) a reconstruction method of the embodiment.

An example of specific calculation speed-up and contrast improvement effect will be described with reference to FIGS. 9 to 11. FIGS. 9(a) to 9(c) are the results of photographing a gel phantom containing four cylinders having different diameters and concentrations with the ultrasound computed tomography scanner and image reconstruction of the sound speed distribution. FIG. 9(a) is a sound speed image obtained by using the straight-ray reconstruction method of the related art without considering the refraction, and FIG. 9(b) is a sound speed image obtained by using the bent-ray reconstruction method of the related art considering the refraction, and FIG. 9(c) is a sound speed image obtained by the straight-ray reconstruction method based on the sinogram corrected for the influence of the refraction of the embodiment that has been described above. In addition, the ART method is used for the reconstruction, and the number of repetitions of the bent-ray reconstruction was set to 1 time. In addition, when generating the reconstructed image of the embodiment of FIG. 9(c), the steps 504 to 508 in FIG. 5(a) are repeated one time.

Figure 10:
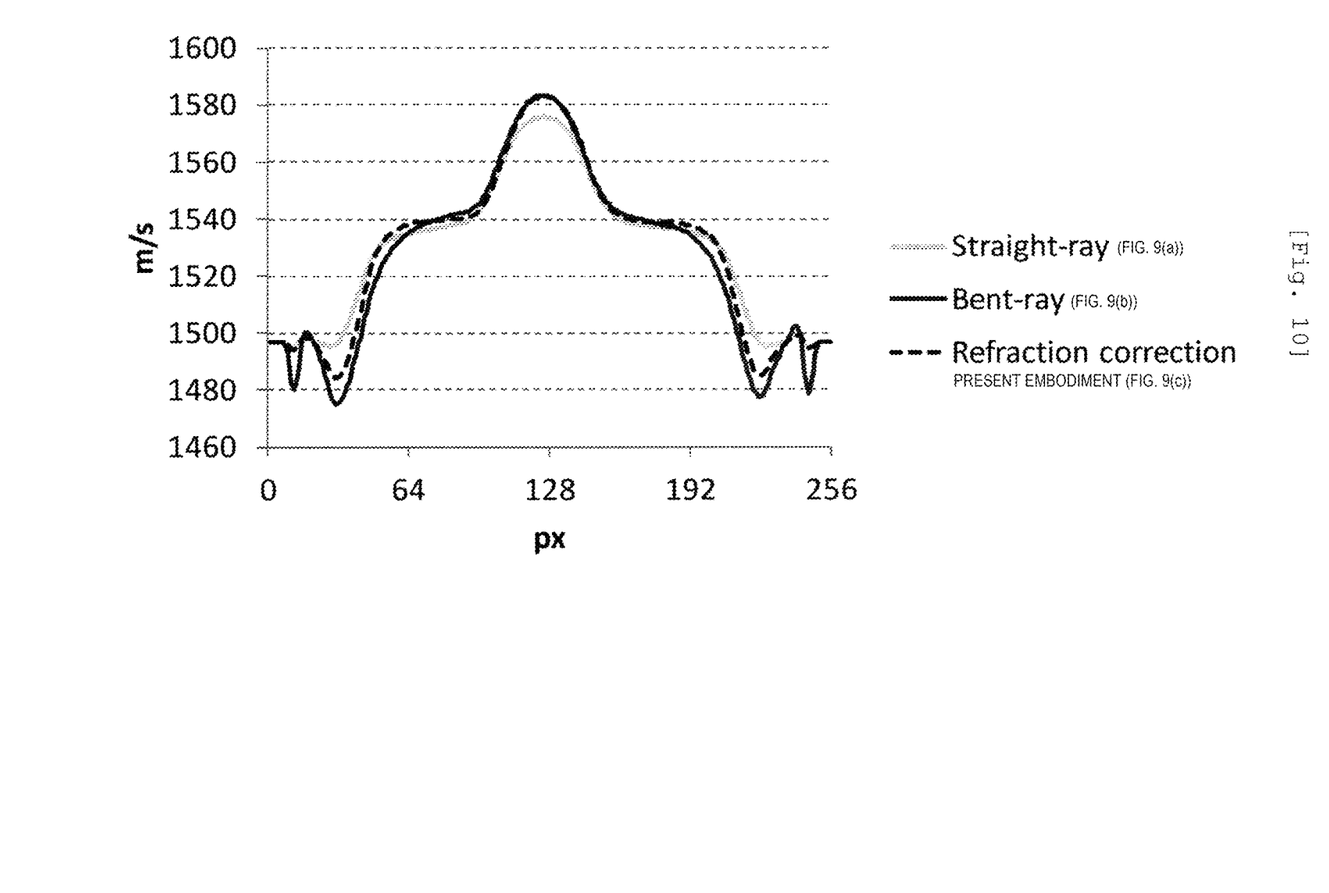
FIG. 10 is a graph illustrating profiles of three sound speed images illustrated in FIG. 9.

FIG. 10 illustrates a profile of a broken line portion of the sound speed images of FIGS. 9(a), 9(b) and 9(c). As is apparent from FIG. 10, by the reconstruction method for performing the correction of the embodiment, it is possible to achieve the same level of contrast improvement as that of the bent-ray reconstruction method of the related art.

Figure 11:
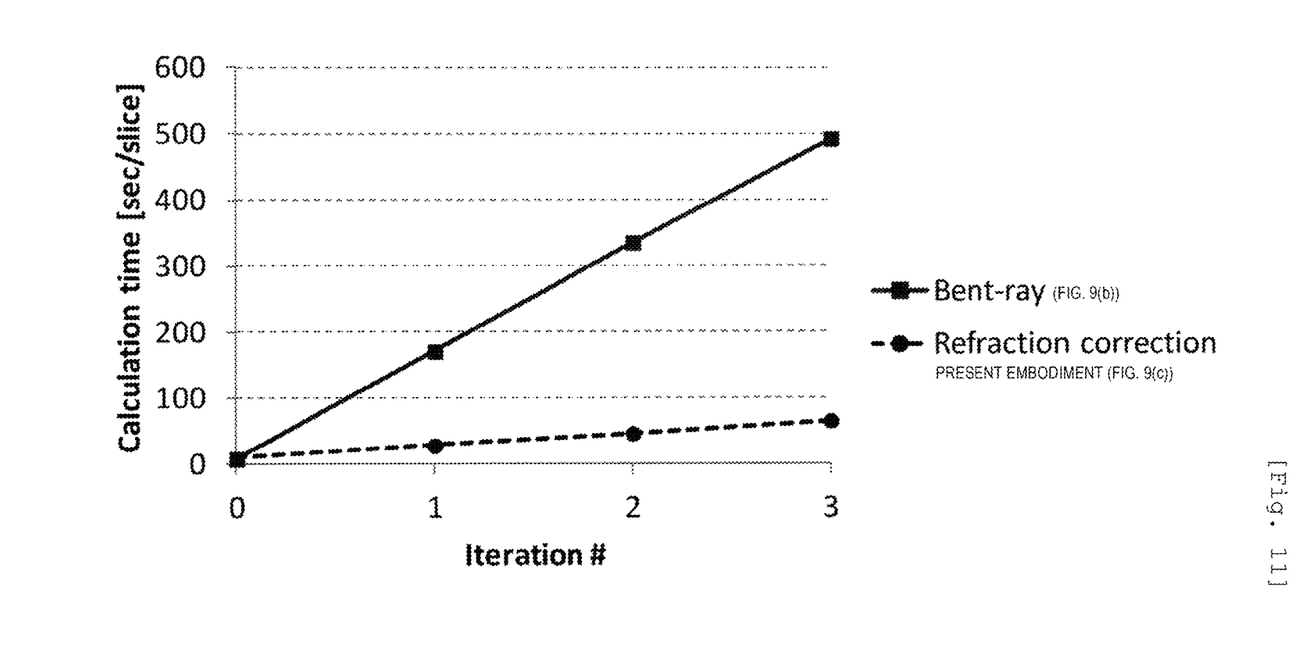
FIG. 11 is a graph illustrating a relationship between computation time and the number of repetitions in a case of generating the sound speed image of one section by the reconstruction method of the embodiment and the bent-ray reconstruction.

Meanwhile, FIG. 11 is a graph illustrating the relationship between the computation time per one section and the number of repetitions. By the reconstruction method for performing the correction of the embodiment, it is possible to realize a calculation speed-up faster than 7 times that of the bent-ray reconstruction method of the related art.

As described above, by using the reconstruction method of the embodiment, it is possible to correct the material property error due to the influence of refraction, and it is possible to provide an image with higher accuracy with less calculation load.

In addition, according to the reconstruction method of the embodiment, since the user can confirm the images before and after the correction, it is possible to switch the presence or absence of application of the correction at any time.

In addition, the data obtaining and the data processing can also be performed by separate devices. For example, in the device configuration of FIG. 2, an image processing device including the signal processing section 7, the storage section 8, and the input and output section 9 is prepared, transmission wave signal data obtained by the control section 6 by driving the ring array 3 is supplied to the image processing device, and here, the above-described reconstruction method can be carried out.

In addition, in the above-described embodiment, a ring array is assumed as the ultrasound transceiver element array 3, but the assumption can be similarly applied to data obtained by a method of rotating a linear probe pair or a two-dimensional oscillator array pair.

In the above-described configuration, parallel beam scan is assumed, but correction can also be similarly performed by fan beam scan. When the path (a) of the refracted wave, the path (b) of the rectilinear wave, and the initial sound speed distribution in the paths are known, it is possible to correct the sinogram by the difference or the ratio of the arrival times of the virtual waves which pass through the paths, and the obtained sinogram may be reconstructed again with a straight-ray model. Otherwise, as a method by which the processing can be performed faster, the arrival time difference sinogram obtained by measurement may be fan-parallel converted, and the present method may be applied to the obtained parallelized sinogram.

In the above-described configuration, the path (a) of the refracted wave is estimated based on the sound speed distribution of a certain section, but a three-dimensional sound speed distribution is calculated from data of a plurality of sections, a path of a three-dimensional wave is estimated, and it is also possible to perform the correction similar to that described above. In this case, for example, by solving the equation (5) in addition to the equation (1), the path (a) of the refracted wave from each transmission position is estimated. Here, z is a direction perpendicular to x and y, and $\phi$ is an angle measured from the y axis to the z axis.

$$\frac{dz}{dy} = \tan\phi = -\frac{d\Delta t}{dz}C_w \qquad \text{[Equation 5]}$$

In addition, the path (a) of the refracted wave is calculated only for the virtual waves which pass through the representative positions, and the path of the virtual wave which passes between the representative positions may be estimated by interpolation. According to this, it is possible to further speed up the image reconstruction operation. For the interpolation, for example, a linear interpolation method or a spline interpolation method may be used.

REFERENCE SIGNS LIST

1 . . . patient, 2 . . . bed, 3 . . . ultrasound transceiver element array (ring array), 3a . . . transmitting element, 3b . . . receiving element, 4 . . . water tank, 5 . . . reserve tank, 6 . . . control section, 7 . . . signal processing section, 8 . . . storage section, 9 . . . input and output section

The invention claimed is:

1. An ultrasound imaging device comprising:
an ultrasound transceiver element array which irradiates an object with ultrasound waves from a plurality of directions, and receives a transmission wave that has been transmitted through the object;
a memory storing a program; and
a processor communicatively coupled to the memory and the ultrasound transceiver element array, the processor configured to execute the program stored in the memory to:
acquire an arrival time difference of the transmission waves by comparing an arrival time in a case where there is the object to an arrival time in a case where there is no object to the ultrasound transceiver element array from a received signal of the ultrasound transceiver element array, and reconstructs a material property distribution image of the inside of the object based on the arrival time difference;
calculate a shortest arrival time of a virtual wave, which is an arrival time of a simulated virtual transmission waves that reach at least one element of the ultrasound transceiver element array through a path that achieves the shortest arrival time calculated based on material property distribution indicated by the material property distribution image;
calculate an arrival time of a virtual wave through a shortest path, which is an the arrival time of a simulated virtual transmission waves that reach the same element through a shortest geometrical path; and
correct the arrival time difference based on the shortest arrival time of the virtual wave and the arrival time of the virtual wave through the shortest path.

2. The ultrasound imaging device according to claim 1, wherein the arrival time difference is corrected by a difference or a ratio between the shortest arrival time of the virtual waved and the arrival time of the virtual wave through the shortest path.

3. An ultrasound imaging device comprising:
an ultrasound transceiver element array which irradiates an object with ultrasound waves from a plurality of directions, and receives a transmission wave that has been transmitted through the object;
a memory storing a program; and
a processor communicatively coupled to the memory and the ultrasound transceiver element array, the processor configured to execute the program stored in the memory to:
acquire an arrival time difference of the transmission waves by comparing an arrival time in a case where there is the object to an arrival time in a case where there is no object from a received signal of the ultrasound transceiver element array, and reconstructs a material property distribution image of the inside of the object based on the arrival time difference; and
correct the arrival time difference, based on a first arrival time calculated on the assumption that the transmission waves reach at least one element of the ultrasound transceiver element array while being refracted in accordance with material property distribution indicated by the material property distribution image, and a second arrival time calculated on the assumption that the transmission waves go straight and reach the same element.

4. The ultrasound imaging device according to claim 1, wherein the processor is further configured to execute the program to calculate the path that achieves the shortest arrival time,
wherein, assuming a first field of view where the material property distribution indicated by the reconstructed material property distribution image of the object exists, a second field of view where the object is not disposed, a plurality of transmitting elements which transmit simulated virtual ultrasound waves to the first field of view and second field of view, and a plurality of receiving elements which receive transmission waves of ultrasound waves that have been transmitted through the first field of view and second field of view, the processor is configured to execute the program to:
obtain a graphical representation of a spatial distribution of the arrival time difference by acquiring distribution of arrival time required for the ultrasound wave transmitted from a position of the plurality of transmitting elements to reach each point in the first field of view and second field of view respectively with respect to the first field of view where there is the material property distribution and the second field of view where the object is not disposed, and by taking a difference therebetween,
differentiate the graphical representation of the distribution of the arrival time difference along a direction perpendicular to an advancing direction of the simulated virtual transmission wave, and
acquire an orientation of the path that achieves the shortest arrival time from the obtained differentiated value of the spatial distribution of the arrival time difference.

5. The ultrasound imaging device according to claim 1, further comprising:
an input/output (I/O) interface which receives from a user whether to apply the correction by the correction section, or whether to repetitively apply the correction and the number of repetitions.

6. The ultrasound imaging device according to claim 1, further comprising:
an input/output (I/O) interface which receives from a user setting of a region of interest at a desired position on the material property distribution image and a desired signal-to-noise ratio (S/N) value in the region of interest.

7. The ultrasound imaging device according to claim 1, wherein the processor is further configured to execute the program to perform the correction after performing fan-parallel conversion with respect to a sinogram which is a data set obtained by collecting the arrival time difference, for each element that configures the ultrasound transceiver element array and for each of the plurality of directions.

8. The ultrasound imaging device according to claim 4, wherein the processor is further configured to execute the program to calculate the path that achieves the shortest arrival time using a plurality of the material property distribution images for different positions.

9. The ultrasound imaging device according to claim 4, wherein the processor is further configured to execute the program to acquire a plurality of paths that pass through representative positions, and calculates a path that passes between the representative positions by interpolation.

10. The ultrasound imaging device according to claim 1, wherein the shortest arrival time of the virtual wave and the arrival time of the virtual wave through the shortest path are calculated with respect to the ultrasound transceiver element array which is virtually disposed.

11. A non-transitory computer readable medium storing an ultrasound image generation program for causing a computer to execute:
a step of acquiring an arrival time difference of the transmission waves by comparing an arrival time in a case where there is the object to an arrival time in a case where there is no object to an ultrasound transceiver element array from a received signal that have been transmitted through the object in the ultrasound element array that has received the transmission wave of the ultrasound wave, and reconstructing a material property distribution image of the inside of the object based on the arrival time difference,
a step of calculating a shortest arrival time of a virtual wave, which is an arrival time of a simulated virtual transmission waves that reach at least one element of the ultrasound transceiver element array through a path that achieves the shortest arrival time calculated based on material property distribution indicated by the material property distribution image;
a step of calculating an arrival time of a virtual wave through a shortest path, which is an the arrival time of a simulated virtual transmission waves that reach the same element through a shortest geometrical path; and
a step of correcting the arrival time difference based on the shortest arrival time of the virtual wave and arrival time of the virtual wave through the shortest path.

* * * * *